United States Patent
Suzuki et al.

(10) Patent No.: US 11,000,463 B2
(45) Date of Patent: May 11, 2021

(54) COSMETIC INCLUDING LIQUID COSMETIC IMPREGNATED INTO IMPREGNATED BODY

(71) Applicant: SHISEIDO COMPANY, LTD., Tokyo (JP)

(72) Inventors: Takahiro Suzuki, Kanagawa (JP); Shoko Ogawa, Kanagawa (JP); Tomoko Ikeda, Kanagawa (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 16/489,715

(22) PCT Filed: Feb. 28, 2018

(86) PCT No.: PCT/JP2018/007417
§ 371 (c)(1),
(2) Date: Aug. 29, 2019

(87) PCT Pub. No.: WO2018/159651
PCT Pub. Date: Sep. 7, 2018

(65) Prior Publication Data
US 2019/0388316 A1  Dec. 26, 2019

(30) Foreign Application Priority Data
Mar. 3, 2017  (JP)  ............................. JP2017-040990

(51) Int. Cl.
*A45D 34/04* (2006.01)
*A61K 8/27* (2006.01)
(Continued)

(52) U.S. Cl.
CPC .............. *A61K 8/37* (2013.01); *A45D 34/042* (2013.01); *A61K 8/064* (2013.01); *A61K 8/27* (2013.01);
(Continued)

(58) Field of Classification Search
None
See application file for complete search history.

(56) References Cited

U.S. PATENT DOCUMENTS 5,340,567 A * 8/1994 Cole .................... A61K 8/27
424/59
10,137,073 B2 * 11/2018 De Lemos ........... A61Q 19/007
(Continued)

FOREIGN PATENT DOCUMENTS

CN   106038325 A   10/2016
EP     2837652 A1    2/2015
(Continued)

OTHER PUBLICATIONS

Millimicron definition supplied by dictionary.com, accessed May 19, 2020. (Year: 2020).*
(Continued)

*Primary Examiner* — Melissa S Mercier
(74) *Attorney, Agent, or Firm* — Rankin, Hill & Clark LLP

(57) ABSTRACT

A cosmetic having high portability including a liquid cosmetic impregnated in an impregnated body is provided, which is excellent in usability and cosmetic effects while keeping an ultraviolet light protection factor (SPF). A liquid cosmetic including an (A) ultraviolet light absorber in an amount of 1 to 10 mass %, and a (B) ultraviolet light scattering agent and a pigment grade titanium dioxide in an amount of 10 to 25 mass % is impregnated in an impregnated body. The liquid cosmetic is taken from the impregnated body by a finger or an applicator to be applied to the skin.

7 Claims, 1 Drawing Sheet

(51) Int. Cl.

| | | |
|---|---|---|
| *A61K 8/29* | (2006.01) | |
| *A61K 8/58* | (2006.01) | |
| *A61K 8/896* | (2006.01) | |
| *A61Q 1/00* | (2006.01) | |
| *A61Q 17/04* | (2006.01) | |
| *A61K 8/37* | (2006.01) | |
| *A61K 8/06* | (2006.01) | |

(52) U.S. Cl.
CPC ............... *A61K 8/29* (2013.01); *A61K 8/585* (2013.01); *A61K 8/896* (2013.01); *A61Q 1/00* (2013.01); *A61Q 17/04* (2013.01); *A61K 2800/10* (2013.01); *A61K 2800/43* (2013.01); *A61K 2800/623* (2013.01); *A61K 2800/87* (2013.01)

(56) References Cited

U.S. PATENT DOCUMENTS

| | | | |
|---|---|---|---|
| 2015/0117931 A1 | 4/2015 | Jung | |
| 2016/0324736 A1 | 11/2016 | Jung | |
| 2016/0331648 A1* | 11/2016 | Park | A61K 8/8111 |
| 2017/0119633 A1 | 5/2017 | Park | |
| 2017/0127799 A1* | 5/2017 | Chung | A45D 33/24 |
| 2018/0360699 A1 | 12/2018 | Jung | |

FOREIGN PATENT DOCUMENTS

| | | | |
|---|---|---|---|
| EP | 3072500 | A1 | 9/2016 |
| EP | 3127530 | A1 | 2/2017 |
| JP | 200312457 | A | 1/2003 |
| JP | 2015512933 | A | 4/2015 |
| JP | 2015120682 | A | 7/2015 |
| JP | 2016130237 | A | 7/2016 |
| JP | 2017002026 | A | 1/2017 |
| KR | 101542917 | B1 | 8/2015 |
| KR | 101609348 | B1 | 4/2016 |
| WO | 2016068300 | A1 | 5/2016 |
| WO | 2016114466 | A1 | 7/2016 |
| WO | 2016200038 | A1 | 12/2016 |

OTHER PUBLICATIONS

Bartholomey E. et al. "A Technical Overview of Cushion Foundation Make-up," SOFW Journal, Dec. 16, 2015, p. 44-46, 48-50, (especially, Abstract, p. 46 "Sunscreen Agents, Shine Control", p. 49 "Formulations, Packaging"), vol. 141, No. 12, SOFWJournal, Germany.

International Search Report dated Apr. 10, 2018 filed in PCT/JP2018/007417.

* cited by examiner

|  | GENERAL | IMPREGNATED BODY |
|---|---|---|
| IN USE | 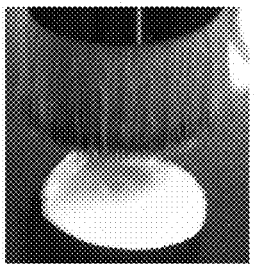 | 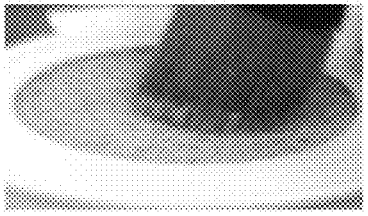 |
| DEPOSITION TO BRUSH | 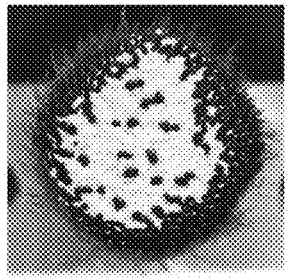 | 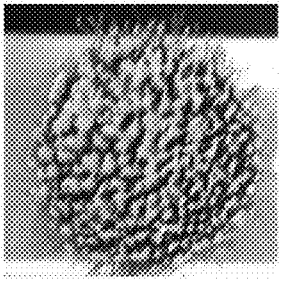 |
| DEPOSITION TO SKIN | 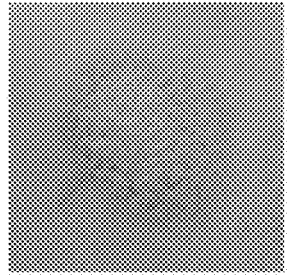 | 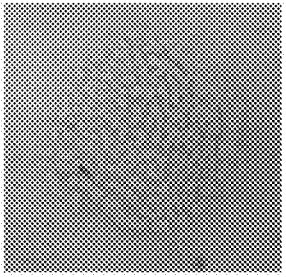 |

COSMETIC INCLUDING LIQUID COSMETIC IMPREGNATED INTO IMPREGNATED BODY

TECHNICAL FIELD

The present invention relates to a cosmetic including a liquid cosmetic that contains specific components mixed therein and is impregnated into an impregnated body, the liquid cosmetic being configured to be taken from the impregnated body and to be applied to the skin.

BACKGROUND ART

Conventionally, a bottle or a tube has been generally used as a container for accommodating a liquid cosmetic. However, a bottle or a tube is difficult to carry for going out, and also makes it difficult to perform a cosmetic behavior easily. For this reason, a cosmetic in a container form such that a liquid cosmetic is impregnated into an impregnated body such as a sponge housed in a compact container, and is applied to the skin with a finger or an applicator upon use has been developed in recent years.

However, a liquid cosmetic often requires addition of a highly polar ultraviolet light absorber or a polar oil serving as the solvent therefor in order to protect the skin of the human body from an ultraviolet light, or in order to inhibit the decomposition or the like of the mixed components by an ultraviolet light. Such a highly polar ultraviolet light absorber, or the like tends to be adsorbed on an impregnated body such as a sponge that is to be impregnated with a liquid cosmetic. This makes it difficult for a liquid cosmetic to be impregnated into an impregnated body to attain or keep an ultraviolet light protection factor (SPF).

Meanwhile, when an inorganic oxide such as a titanium oxide is added in a too large amount as an ultraviolet light scattering agent in order to obtain a high ultraviolet light protection factor (SPF), the flowability of the liquid cosmetic is impaired. As a result, it becomes difficult to impregnate the liquid cosmetic into an impregnated body in a manufacturing process, and it becomes difficult to take the liquid cosmetic from the impregnated body for use. Accordingly, it becomes difficult to apply a sufficient amount of the liquid cosmetic onto the skin. Further, spreading is slow, so that uniform application to the skin becomes difficult, unfavorably resulting in a lack of smooth finish even after application.

Thus, for the cosmetic such that a liquid cosmetic is taken from an impregnated body to be applied onto the skin, in order to keep a high ultraviolet light protection factor (SPF) while minimizing the mixing amount of a highly polar ultraviolet light absorber, it is important to study the proper kind and amount for an ultraviolet light absorber and an ultraviolet light scattering agent mixable in the liquid cosmetic.

[PTL 1] Japanese Translation of PCT Application No. 2015-512933
[PTL 2] Japanese Patent Application Publication No. 2015-120682

SUMMARY OF INVENTION

Technical Problem

It is an object of the present invention to provide a cosmetic including a liquid cosmetic impregnated into an impregnated body, the liquid cosmetic being to be taken from such an impregnated body, and to be applied to the skin, the cosmetic being excellent in usability and cosmetic effects, while keeping a high ultraviolet light protection factor (SPF).

Solution to Problem

In order to solve the problem, the present inventors conducted a study. As a result, the present inventors found the following: 1 to 10 mass % of an (A) ultraviolet light absorber, and 10 to 25 mass % of a (B) ultraviolet light scattering agent and a pigment grade titanium oxide are mixed to a liquid cosmetic to be impregnated in an impregnated body; as a result, a high ultraviolet protection factor (SPF) can be obtained, and the usability and the cosmetic effects are excellent. This has led to the completion of the present invention.

Namely, the present invention relates to a cosmetic characterized by including: a liquid cosmetic including an (A) ultraviolet light absorber in an amount of 1 to 10 mass %, and a (B) ultraviolet light scattering agent and a pigment grade titanium oxide in an amount of 10 to 25 mass %; and an impregnated body impregnated with the liquid cosmetic, the liquid cosmetic being configured to be taken from the impregnated body with a finger or an applicator for being applied to the skin.

Further, the present invention relates to the cosmetic, characterized in that the (A) ultraviolet light absorber is octylmethoxy cinnamate.

Still further, the present invention relates to the cosmetic, characterized in that the (B) ultraviolet light scattering agent is a fine grain titanium oxide or a fine grain zinc oxide.

Furthermore, the present invention relates to the cosmetic, characterized in that the liquid cosmetic is a water-in-oil emulsified cosmetic including a silicone surfactant.

Still furthermore, the present invention relates to the cosmetic, characterized in that the silicone surfactant at least includes bis-butyl dimethicone polyglyceryl-3.

Further, the present invention is the cosmetic, characterized in that the impregnated body is a fiber body, a foamed body, or a porous body.

Still further, the present invention is the cosmetic, characterized in that the impregnated body impregnated with the liquid cosmetic is housed in a compact container having airtightness.

Furthermore, the present invention is the cosmetic, characterized in that the applicator is a brush.

Advantageous Effects of Invention

In accordance with a cosmetic of the present invention, with the cosmetic including a liquid cosmetic impregnated into an impregnated body, the liquid cosmetic being taken from such an impregnated body to be applied to the skin, excellent usability and cosmetic effects can be obtained while attaining a high ultraviolet light protection factor (SPF).

BRIEF DESCRIPTION OF DRAWINGS

FIG. 1 is a view (drawing substitute photograph) showing the effects of taking a liquid cosmetic from an impregnated body using a brush.

DESCRIPTION OF EMBODIMENTS

A cosmetic according to the present invention is characterized by including: an (A) ultraviolet light absorber in an amount of 1 to 10 mass %, and a (B) ultraviolet light scattering agent and a pigment grade titanium oxide in an amount of 10 to 25 mass %; and an impregnated body impregnated with the liquid cosmetic, the liquid cosmetic being configured to be taken from the impregnated body with a finger or an applicator for being applied to the skin.

Herein, the behavior of taking the liquid cosmetic from the impregnated body by an applicator includes taking or scooping the liquid cosmetic by putting a puff, a brush, or the like on the impregnated body for transfer therein. When the liquid cosmetic is tried to be directly taken by an applicator such as a puff or a brush, the liquid cosmetic is attached in a large amount only on a part of the applicator, which makes it difficult for the liquid cosmetic to be uniformly applied to the skin (photograph on the left side of FIG. 1). When the liquid cosmetic is taken from the impregnated body impregnated with the liquid cosmetic using an applicator, the liquid cosmetic can be taken from the wide surface of the impregnated body. Accordingly, the liquid cosmetic can be uniformly attached onto the entire surface of the applying part of the applicator, which enables even and uniform application of the liquid cosmetic to the skin (photograph on the right side of FIG. 1).

In the case using a brush for the applicator, when application is performed in such a manner that the tip of the brush is patted on the skin, the liquid cosmetic can be applied in equal amounts little by little to the skin irrespective of the viscosity of the liquid cosmetic. For this reason, make-up can be finished without thick and uneven application (photograph on the right side of FIG. 1).

As the (A) ultraviolet light absorber for use in the present invention, those usually usable for a cosmetic or a skin external preparation can be used. Examples thereof may include triazine ultraviolet light absorbers (e.g., bisresorcinyl triazine); octyl triazone (2,4,6-tris[4-(2-ethylhexyloxy-carbonyl)anilino]1,3,5-triazine); benzoic acid ultraviolet light absorbers (e.g., para-aminobenzoic acid (hereinafter, abbreviated as PABA), PABA monoglycerin ester, N,N-dipropoxy PABA ethyl ester, N,N-diethoxy PABA ethyl ester, N,N-dimethyl PABA butyl ester, N,N-dimethyl PABA ethyl ester); anthranilic acid ultraviolet light absorber (e.g., homomenthyl-N-acetyl anthranilate); salicylic acid ultraviolet light absorbers (e.g., amyl salicylate, menthyl salicylate, homomenthyl salicylate, octyl salicylate, phenyl salicylate, benzyl salicylate, and p-isopropanol phenyl salicylate); cinnamic acid ultraviolet light absorber (e.g., ethylhexyl methoxycinnamate, octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, octyl-p-methoxy cinnamate (2-ethylhexyl-p-methoxy cinnamate), 2-ethoxy ethyl-p-methoxy cinnamate, cyclohexyl-p-methoxy cinnamate, ethyl-α-cyano-β-phenyl cinnamate, 2-ethylhexyl-α-cyano-β-phenyl cinnamate, glycerylmono-2-ethyl hexanoyl-di-paramethoxy cinnamate); benzophenone ultraviolet light absorbers (e.g., 2,4-dihydroxy benzophenone, 2,2'-dihydroxy-4-methoxy benzophenone, 2,2'-dihydroxy-4,4'-dimethoxy benzophenone, 2,2',4,4'-tetrahydroxy benzophenone, 2-hydroxy-4-methoxybenzophenone, 2-hydroxy-4-methoxy-4'-methylbenzophenone, 2-hydroxy-4-methoxy benzophenone-5-sulfonate, 4-phenyl benzophenone, 2-ethylhexyl-4'-phenyl-benzophenone-2-carboxylate, 2-hydroxy-4-n-octoxybenzophenone, and 4-hydroxy-3-carboxybenzophenone); 3-(4'-methyl benzylidene)-d,l-camphor, 3-benzylidene-d,l-camphor; 2-phenyl-5-methylbenzoxazole; 2,2'-hydroxy-5-methylphenylbenzotriazole; 2-(2'-hydroxy-5'-t-octylphenyl)benzotriazole; 2-(2'-hydroxy-5'-methylphenyl)benzotriazole; bis-ethylhexyloxyphenol methoxyphenyl triazine; dibenzalazine; dianisoyl methane; 4-methoxy-4'-t-butyl-dibenzoyl-methane; 5-(3,3-dimethyl-2-norbornylidene)-3-pentane-2-one, methylene bis-benzotriazolyl tetramethylbutylphenol, 4,4-diarylbutadiene, and octocrylene.

Out of these, cinnamic acid ultraviolet light absorbers of high polar oils such as octyl cinnamate, ethyl-4-isopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, octyl methoxycinnamate, 2-ethoxyethyl-p-methoxy cinnamate, cyclohexyl-p-methoxy cinnamate, ethyl-α-cyano-β-phenyl cinnamate, and 2-ethylhexyl-α-cyano-β-phenyl cinnamate are preferable because of the high ultraviolet light protection factor (SPF).

The mixing amount of the (A) ultraviolet light absorber is set at 1 to 10 mass % based on the amount of the liquid cosmetic. This is because the following reason. When the mixing amount is less than 1 mass %, a sufficient ultraviolet light protection factor (SPF) may not be obtainable. On the contrary, when the mixing amount exceeds 10 mass %, the feel of slipping on the skin always remains upon application on the skin, resulting in inferior usability.

The (B) ultraviolet light scattering agent and the pigment grade titanium dioxide exert an effect of scattering or blocking an ultraviolet light. As the ultraviolet light scattering agent, fine grain titanium oxide or fine grain zinc oxide, or a powder of the mixture thereof is preferably used. Further, as the pigment grade titanium dioxide, titanium dioxide with a relatively large grain size, to be commonly mixed in a cosmetic or a skin external preparation as a pigment is used.

A fine grain titanium oxide is fine grain titanium oxide with an average grain size of 0.1 m or less (the average grain size has no particular restriction on the lower limit, and is generally about 30 nm) commonly used for an external composition such as a cosmetic, and can be manufactured by a general method such as a sulfuric acid method or a chlorine method. Alternatively, a commercially available product can also be used. Examples of the commercially available fine grain titanium oxide may include SIV series, TTO-55 series, and TTO-S series (manufactured by ISHIHARA SANGYO KAISYA Ltd.), and MT-100TV, MT-500V, and MT-01 (manufactured by TAYCA Corporation).

A fine grain zinc oxide is preferably a fine grain zinc oxide with an average grain size of 0.1 µm or less (the average grain size has no particular restriction on the lower limit, and is generally about 30 nm) commonly used for an external composition such as a cosmetic, and can be manufactured by a general method such as a France method or an America method. Alternatively, a commercially available product can also be used. Examples of the commercially available fine grain zinc oxide may include FINEX-25, FINEX-50, and FINEX-75 (manufactured by SAKAI Chemical Industry Co., Ltd.), ZnO 350 (manufactured by Sumitomo Osaka Cement Co., Ltd.), ZINCOX SUPER-10, ZINCOX SUPER-20R, ZINCOX SUPER-30, and ZINCOX CP-1 (manufactured by Hakusui Chemical Industries, Ltd.), Z-COTE (manufactured by Sun Smart), and MZ-500 and MZ-700 (manufactured by TAYCA Corporation).

For an ultraviolet light scattering agent, a fine grain titanium oxide or a fine grain zinc oxide is used as abase material, and the surface thereof may be subjected to a hydrophobization treatment. Examples of the methods of the surface hydrophobization treatment include a silicone treatment with methyl hydrogen polysiloxane, methyl polysiloxane, or the like; a fluorine treatment with perfluoroalkyl phosphate, perfluoro alcohol, or the like; an amino acid treatment with N-acyl glutamate or the like; other than these, a lecithin treatment; a metallic soap treatment; a fatty acid treatment; an alkyl phosphoric acid ester treatment; and the like.

The pigment grade titanium dioxide denotes a titanium dioxide having an average grain size of 0.1 to 0.5 μm, and providing a white outward appearance color by light scattering. The pigment grade titanium dioxide for use in the present invention may be subjected to a coating treatment. As the treatment method, a hydrophobization treatment such as a silicon treatment, or the like can be mentioned, although the treatment method has no particular restriction.

The mixing amount of the (B) ultraviolet light scattering agent and the pigment grade titanium dioxide is set at 10 to 25 mass % based on the amount of the liquid cosmetic. This is due to the following reason: when the mixing amount is less than 10 mass %, a sufficient ultraviolet light protection factor (SPF) may not be obtainable; on the contrary, when the mixing amount exceeds 25 mass %, spreading is slow upon application to the skin, undesirably resulting in powdery finish.

The liquid cosmetic can be not only an oily cosmetic obtained by mixing a powder component, or the like to a liquid oil component, but also a water-in-oil emulsified cosmetic obtained by mixing a water component (in an amount of 10 to 50 mass % based on the amount of the liquid cosmetic).

As a silicone surfactant for use in the present invention, an emulsifier generally mixable to a water-in-oil emulsified composition can be mixed. As such an emulsifier, a hydrophobic emulsifier (HLB of 7 or less) is preferably used. Examples thereof may include polyether silicones such as cetyl dimethicone copolyol [e.g., "ABIL EM90" (manufactured by Goldschmidt Co.)], and polyether modified silicone [e.g., "KF 6017" (manufactured by Shin-Etsu Chemical Co., Ltd.)]; and polyglycerin type silicones such as polyglycerin modified silicone, alkyl-comodified polyglycerin-modified silicone. In the present invention, one or two or more surfactants with a HLB of 7 or less can be used.

Further, when double-end-siliconized polyethylene glycol such as bis-butyl dimethicone polyglyceryl-3 ["KF-6109" (manufactured by Shin-Etsu Chemical Co., Ltd.)] is mixed out of the silicone surfactants, a high ultraviolet light protection factor (SPF) can be obtained. Even when an inorganic oxide such as titanium oxide is mixed in a large amount, the flowability of the liquid cosmetic is not impaired. Further, the mixing amount of the double-end-siliconized polyethylene glycol is preferably set at 5 mass % or less based on the amount of the liquid cosmetic. This is due to the following: when the mixing amount exceeds 5 mass %, the heavy feeling in spreading derived from the activator is caused upon application to the skin, resulting in inferior usability.

Examples of the impregnated bodies for impregnating the liquid cosmetic thereinto include a nonwoven fabric formed of a single or mixed material such as a resin, pulp, or cotton, a resin-treated fiber body, a foamed body such as a sponge, a porous body including a continuous structure, and the like. Further, examples of the material may include NBR (acrylonitrile butadiene rubber), SBR (styrene butadiene rubber), NR (natural rubber), urethane, nylon, polyolefin, polyester, EVA (ethylene vinyl acetate), PVA (polyvinyl alcohol), silicone, and elastomer. The material for the impregnated body is preferably hydrophilic, but is not limited to the materials so long as the material is an impregnated body capable of including the contents.

Examples of the applicator for taking the liquid cosmetic from the impregnated body, and applying the liquid cosmetic to the skin include a sponge, a puff, a chip, a brush, or the like which are to be commonly used for applying the liquid cosmetic to the skin.

The oil component to be mixed in the oil phase of the emulsified cosmetic has no particular restriction so long as it is an oil component generally mixable in a cosmetic. Examples thereof may include fats and oils, waxes, hydrocarbon oil, higher fatty acid, higher alcohol, synthetic ester oil, and silicone oil.

Examples of fats and oils may include liquid fats and oils such as avocado oil, *camellia* oil, Evening Primrose oil, Turtle oil, macadamia nut oil, corn oil, mink oil, olive oil, rapeseed oil, egg-yolk oil, sesame oil, persic oil, wheat germ oil, sasanqua oil, castor oil, linseed oil, safflower oil, cotton seed oil, *perilla* oil, soybean oil, peanut oil, tea seed oil, Kaya oil, rice bran oil, China tung oil, Japan tung oil, jojoba oil, germ oil, triglycerin, glycerin trioctanoate, and glycerin triisopalmitate; and solid fats and oils such as cacao butter, coconut oil, horse fat, hardened coconut oil, palm oil, beef tallow, mutton tallow, hardened beef tallow, palm kernel oil, lard, beef bone fat, Japan tallow kernel oil, hardened oil, beef leg tallow, Japan tallow, and hardened castor oil.

Examples of the wax may include beeswax, candelilla wax, cotton wax, carnauba wax, bayberry wax, insects wax, spermaceti, montan wax, bran wax, lanolin, kapok wax, lanolin acetate, liquid lanolin, sugarcane wax, lanolin fatty acid isopropyl, hexyl laurate, reduced lanolin, jojoba wax, hard lanolin, shellac wax, POE lanolin alcohol ether, POE lanolin alcohol acetate, POE cholesterol ether, lanolin fatty acid polyethylene glycol, and POE hydrogenated lanolin alcohol ether.

Examples of hydrocarbon may include liquid paraffin, ozokerite, squalene, pristane, paraffin, ceresin, squalane, Vaseline, and microcrystalline wax.

Examples of higher fatty acid may include lauric acid, myristic acid, palmitic acid, stearic acid, behenic acid, oleic acid, 12-hydroxystearic acid, undecylenic acid, tall oil acid, isostearic acid, linolic acid, linolenic acid, eicosapentaenoic acid (EPA), and docosahexaenoic acid (DHA).

Examples of higher alcohol may include linear alcohols such as lauryl alcohol, cetyl alcohol, stearyl alcohol, behenyl alcohol, myristyl alcohol, oleyl alcohol, and cetostearyl alcohol; and branched alcohols such as monostearyl glycerin ether (batyl alcohol), 2-decyltetradecinol, lanolin alcohol, cholesterol, phytosterol, hexyl dodecanol, isostearyl alcohol, and octyl dodecanol.

Examples of synthetic ester oil may include isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethylhexylate, dipentaerythritol fatty acid ester, N-alkyl glycol monoisostearate, neopentyl glycol dicaprylate, diisostearyl malate, glycerin di-2-heptylundecanoate, trimethylolpropane tri-2-ethylhexylate, trimethylolpropane triisostearate, pentaerythritol tetra-2-ethylhexylate, glycerin tri-2-ethylhexylate, trimethylolpropane triisostearate, cetyl 2-ethylhexanoate, 2-ethylhexylpalmitate, glycerin trimyristate, tri-2-heptylundecanoic glyceride, castor oil fatty acid methyl ester, oleic acid oil, acetoglyceride, 2-heptylundecyl palmitate, diisopropyl adipate, 2-octyldodecyl N-lauroyl-L-glutamate, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, ethyl acetate, butyl acetate, amyl acetate, triethyl citrate, and crotamiton (C13H17NO).

Examples of silicone oil may include chain polysiloxanes such as dimethyl polysiloxane, methyl phenyl polysiloxane, and methyl hydrogen polysiloxane; cyclic polysiloxanes such as decamethyl polysiloxane, dodecamethyl polysiloxane, and tetramethyl tetrahydrogen polysiloxane; and silicone resin or silicone rubber that forms a three-dimensional network structure. In the present invention, one or two or more emulsifiers with a HLB of 7 or less can be used.

Examples of aqueous components include water and a water-soluble component. Examples of the water-soluble component may include lower alcohols, a moisturizing agent, and a water-soluble high polymer (natural, semi-synthetic, synthetic, or inorganic).

Examples of the lower alcohol may include ethanol, propanol, butanol, pentanol, and hexanol.

Examples of the moisturizing agent may include glycerin, diethylene glycol, butylene glycol, polyethylene glycol, hexylene glycol, xylytol, sorbitol, maltitol, chondroitin sulfate, hyaluronic acid, mucoitin sulfate, chalonic acid, atelocollagen, elastin, amino acid, nucleic acid, cholesteryl-12-hydroxystearate, sodium lactate, bile acid salt, dl-pyrrolidonecarboxylic acid salt, short-chain soluble collagen, diglycerin (EO)PO adduct, Chestnut rose extracts, *Achillea millefolium* extracts, and melilot extracts.

Examples of the natural water-soluble high polymer may include plant origin water-soluble high polymers such as gum arabic, gum tragacanth, galactan, guar gum, locust bean gum, tamarind gum, carob gum, gum karaya, carrageenan, pectin, agar, quince seed (marmelo), algae colloid (brown algae extracts), starch (rice, corn, potato, or wheat), and glycyrrhizic acid; microbic origin water-soluble high polymers such as xanthan gum, dextran, succinoglycan, and pullulan; and animal origin water-soluble high polymers such as collagen, casein, albumin, and gelatin.

Examples of the semi-synthetic water-soluble high polymer may include starch type water-soluble high polymers such as carboxymethyl starch, and methyl hydroxypropyl starch; cellulose type water-soluble high polymers such as methyl cellulose, nitrocellulose, ethyl cellulose, methyl hydroxypropyl cellulose, hydroxyethyl cellulose, sodium cellulose sulfate, hydroxypropyl cellulose, carboxymethyl cellulose (CMC), crystal cellulose, and cellulose powder; and alginic acid type water-soluble high polymers such as sodium alginate, and propylene glycol alginate.

Examples of the synthetic water-soluble high polymer may include vinyl type water-soluble high polymers such as polyvinyl alcohol, polyvinyl methyl ether, polyvinyl pyrrolidone, and carboxyvinyl polymer (Carbopol); polyoxyethylene type water-soluble polymers such as polyethylene glycol 20,000, polyethylene glycol 4,000,000, and polyethylene glycol 600,000; copolymer type water-soluble high polymers such as polyoxyethylene/polyoxypropylene copolymer; acrylic water-soluble high polymers such as sodium polyacrylate, polyethyl acrylate, and polyacrylamide, and additionally, polyethyleneimine, and cation polymers.

Examples of the inorganic water-soluble high polymer may include bentonite, magnesium aluminum silicate (veegum), laponite, hectorite, and silicic acid anhydride.

As the powder component, either of hydrophobic powder or hydrophilic powder can be used, and hydrophobic powder is preferable. The hydrophobic powder include not only the powder which itself is hydrophobic, but also a hydrophobized powder obtained by subjecting the powder surface to a hydrophobization treatment even for a hydrophilic powder or the like.

Specific examples of the hydrophobic powder may include organic powders such as polyamide resin powder (nylon powder), polyethylene powder, polymethyl methacrylate powder, polystyrene powder, styrene and acrylic acid copolymer resin powder, benzoguanamine resin powder, polytetrafluoride ethylene powder, and cellulose powder; and silicone powders such as trimethyl silsesquioxane powder.

Examples of the powder component of the hydrophobized powder may include inorganic powders such as talc, kaolin, mica, sericite, muscovite, phlogopite, synthetic mica, lepidolite, biotite, lithia mica, vermiculite, magnesium carbonate, calcium carbonate, aluminum silicate, barium silicate, calcium silicate, magnesium silicate, strontium silicate, tungstate metal salt, magnesium, silica, zeolite, barium sulfate, sintered calcium sulfate (burnt gypsum), calcium phosphate, fluoroapatite, hydroxyapatite, ceramic powder, metallic soaps (such as zinc myristate, calcium palmitate, and aluminum stearate), and boron nitride; inorganic white pigments such as titanium dioxide and zinc oxide; inorganic red pigments such as iron oxide (red iron oxide) and iron titanate; inorganic brown pigments such as γ-iron oxide; inorganic yellow pigments such as yellow iron oxide and ocher; inorganic black pigments such as black iron oxide, carbon black, and low-order titanium dioxide; inorganic purple pigments such as mango violet, and baltic violet; inorganic green pigments such as chromium oxide, chromium hydroxide, and cobalt titanate; inorganic blue pigments such as ultramarine and deep blue; pearl pigments such as titanium dioxide-coated mica, titanium dioxide-coated bismuth oxychloride, titanium dioxide-coated talc, colored titanium dioxide-coated mica, bismuth oxychloride, and fish scale foil; and metal powder pigments such as aluminum powder and copper powder. As the method for subjecting the powder components to a hydrophobization treatment, any hydrophobization treatment method is acceptable so long as it is a method capable of imparting water repellency, and the method is not limited. For example, general surface treatment methods such as a gas phase method, a liquid phase method, an autoclave method, and a mechanochemical method can be used. The hydrophobizing agent is not particularly limited and examples thereof include fatty acid dextrin-treated powder, trimethyl siloxysilicate-treated powder, fluorine-modified trimethyl siloxysilicate-treated powder, methyl phenyl siloxysilicate-treated powder, fluorine-modified methyl phenyl siloxysilicate-treated powder, powders treated with low viscosity to high viscosity oily polysiloxanes such as dimethyl polysiloxane, diphenyl polysiloxane, and methyl phenyl polysiloxane, gum-like polysiloxane-treated powder, methyl hydrogen polysiloxane-treated powder, fluorine-modified methyl hydrogen polysiloxane-treated powder, treated powder treated with organic silyl compounds such as methyl trichlorosilane, methyl trialkoxysilane, hexamethyl disilane, dimethyl dichlorosilane, dimethyl dialkoxysilane, and trimethyl chlorosilane trimethylalkoxysilane, or fluorine-substituted products thereof, treated powder treated with organic modified silanes such as ethyl trichlorosilane, ethyl trialkoxysilane, propyl trichlorosilane, propyl trialkoxysilane, hexyl trichlorosilane, hexyl trialkoxysilane, long-chain alkyl trichlorosilane, and long-chain alkyl triethoxysilane, or a fluorine-substituted products thereof, amino-modified polysiloxane-treated powder, fluorine-modified polysiloxane treated powder, and fluoroalkyl phosphate-treated powder.

Examples of other mixable components than the exemplified components may include antiseptic agents (such as ethyl paraben and butyl paraben); antiflash agent (e.g., glycyrrhizinic acid derivatives, glycyrrhetinic acid derivatives, salicylic acid derivatives, hinokitiol, zinc oxide, and allantoin); skin whitening agents (e.g., *Saxifraga* Sarmentosa extract and arbutin); various extracts (e.g., phellodendron bark, *Coptis japonica*, lithospermum root, Chinese peony, swertia herb, birch, sage, loquat, carrot, aloe, mallow, iris, grape, *coix* seed, dishcloth gourd, lily, saffron, Cnidium Rhizome, ginger, *hypericum*, ononis, garlic, chilli pepper, citrus unshiu peel, *Angelica acutiloba*, and seaweed); activator agents (e.g., royal jelly, photosensitive pigments, and cholesterol derivatives); blood circulation promoters (e.g., nonanoic acid vanillylamide, nicotinic acid benzyl ester, nicotinic acid β-butoxyethyl ester, capsaicin, zingerone, cantharides tincture, ichthammol, tannic acid, α-borneol, tocopherol nicotinate, inositol hexanicotinate, cyclandelate, cinnarizine, tolazoline, acetylcholine, verapamil, cepharanthine, and y-orizanol); antiseborrheic agents (e.g., sulfur and thianthol); anti-inflammatory agents (e.g., tranexamic acids; thiotaurine; and hypotaurine); and ultraviolet light absorbers. However, the present invention is not limited to these examples.

The cosmetic of the present invention can be configured in a container form suitable for carrying by allowing an impregnated body impregnated with a liquid cosmetic to be housed in a compact container having airtightness.

EXAMPLES

The present invention will be further described below in details by way of examples. However, the examples do not limit the present invention. The numerical values in Tables represent the numeric values in terms of mass % unless otherwise stated.

As for the ultraviolet light protection effect, the absorbance at 290 to 400 nm was determined using a spectrophotometer ("U-4100": manufactured by Hitachi Hight-Technologies Corporation). SPF was estimated from the integral value of the absorbance, and judged in accordance with the following standard: A: 50 or more, B: 40 or more and less than 50, C: 30 or more and less than 40, and D: less than 30. The used substrate is a skin substitute membrane obtained by spraying a white molten alumina abrasive material, FUJIRANDOM WA grain size #16 (manufactured by Fuji Manufacturing Co., Ltd.) onto one side surface of an ACRYLITE 000 (manufactured by MITSUBISHI RAYON CO., LTD.) using a sandblast device PNEUMA BLASTER (manufactured by Fuji Manufacturing Co., Ltd.), and subjecting the sprayed substrate to a sandblast processing, followed by cutting into 50-mm square pieces.

The present cosmetic was applied and spread onto the skin substitute membrane by a finger with a fingerstall so that the applied amount be at 2.00 mg/cm$^2$. Then, the absorbance at 290 to 400 nm was measured by a spectrophotometer. For every substrate of the skin substitute membrane coated with the liquid cosmetic, a total of five regions of the vicinity of the center, and the vicinity of the midpoints between the center and the four corners were measured. The absorbance was determined from the average of the measured values measured for a total of three substrates.

As for each of the "finish" and "usability" of the evaluation items, a use test by a panel of ten panelists was conducted. For the use test, a brush was used as an applicator. The impregnated body impregnated with the liquid cosmetic was applied to the skin while being included in an amount of 0.2 g in the brush. As the application method, the cosmetic was deposited on the cheek in a patting manner with the tip of the brush, and was spread until the cosmetic is absorbed along the contour of the face. The number of panelists who considered the finish of the whole cheek and the spreadability of the cosmetic as being good was expressed as the score for evaluation. The standards are as follows: A: 9 points or more, B: 6 to 8 points, C: 3 to 5 points, and D: 2 points or less. The scores A to C were determined as acceptable, and D was determined as inacceptable.

TABLE 1

| Classification | Component | Example 1 | Example 2 | Example 3 | Example 4 | Example 5 | Example 6 | Comparative Example 1 | Comparative Example 2 | Comparative Example 3 | Comparative Example 4 | Comparative Example 5 | Comparative Example 6 | Comparative Example 7 | Comparative Example 8 |
|---|---|---|---|---|---|---|---|---|---|---|---|---|---|---|---|
| Volatile silicone oil component | Cyclopentasiloxane | 55 | 45 | 38 | 64 | 54 | 47 | 50 | 33 | 65 | 48 | 60 | 69 | 34 | 43 |
| (A) Ultraviolet light absorber | Octyl methoxy cinnamate | 10 | 10 | 10 | 1 | 1 | 1 | 15 | 15 | 0 | 0 | 10 | 1 | 10 | 1 |
| Silicone surfactant | PEG-10 dimethicone | 2 | 2 | 2 | 2 | 2 | 2 | 2 | 2 | 2 | 2 | 2 | 2 | 2 | 2 |
|  | Bis-butyl dimethicone polyglyceryl-3 | 1 | 1 | 1 | 1 | 1 | 1 | 1 | 1 | 1 | 1 | 1 | 1 | 1 | 1 |
| Water | Water | 20 | 20 | 20 | 20 | 20 | 20 | 20 | 20 | 20 | 20 | 20 | 20 | 20 | 20 |
| (B) Ultraviolet light scattering agent | Hydrophobized fine grain titanium oxide | 3 | 13 | 5 | 3 | 13 | 5 | 3 | 5 | 3 | 5 | 0 | 0 | 20 | 20 |
| Pigment grade titanium oxide | Pigment grade titanium oxide | 7 | 7 | 20 | 7 | 7 | 20 | 7 | 20 | 7 | 20 | 5 | 5 | 10 | 10 |

TABLE 1-continued

| Classification | Component | Example 1 | Example 2 | Example 3 | Example 4 | Example 5 | Example 6 | Comparative Example 1 | Comparative Example 2 | Comparative Example 3 | Comparative Example 4 | Comparative Example 5 | Comparative Example 6 | Comparative Example 7 | Comparative Example 8 |
|---|---|---|---|---|---|---|---|---|---|---|---|---|---|---|---|
| Coloring material | Hydrophobized iron oxide (red) | 0.6 | 0.6 | 1.35 | 0.6 | 0.6 | 1.35 | 0.6 | 1.35 | 0.6 | 1.35 | 0.6 | 0.6 | 0.9 | 0.9 |
| | Hydrophobized iron oxide (yellow) | 1.39 | 1.39 | 2.62 | 1.39 | 1.39 | 2.62 | 1.39 | 2.62 | 1.39 | 2.62 | 1.39 | 1.39 | 2.08 | 2.08 |
| | Hydrophobized iron oxide (black) | 0.01 | 0.01 | 0.03 | 0.01 | 0.01 | 0.03 | 0.01 | 0.03 | 0.01 | 0.03 | 0.01 | 0.01 | 0.02 | 0.02 |
| Total of (B) components | | 10 | 20 | 25 | 10 | 20 | 25 | 10 | 25 | 10 | 25 | 5 | 5 | 30 | 30 |
| | Total | 100 | 100 | 100 | 100 | 100 | 100 | 100 | 100 | 100 | 100 | 100 | 100 | 100 | 100 |
| Evaluation results | UV light protection effect<br>A: 50 or more<br>B: 40 or more and less than 50<br>C: 30 or more and less than 40<br>D: less than 30 | B | A | A | C | C | C | A | A | D | D | C | D | A | A |
| | Finish (evaluation by general panel N = 10)<br>A: 9 points or more<br>B: 6 to 8 points<br>C: 3 to 5 points<br>D: 2 points or less | A | B | B | A | B | C | A | D | C | D | A | B | D | D |
| | Usability (evaluation by general panel N = 10)<br>A: 9 points or more<br>B: 6 to 8 points<br>C: 3 to 5 points<br>D: 2 points or less | B | B | A | A | B | C | D | C | B | C | D | D | D | D |

As shown in Table 1, for each of Examples 1 to 6 in which a to 10 mass % of the (A) ultraviolet light absorber and 10 to 25 mass % of the (B) ultraviolet light scattering agent and the pigment grade titanium dioxide were mixed, the ultraviolet light protection effect (SPF) was 30 or more, and scores of A to C were able to be given in evaluation of the usability. However, when the amount of the (A) ultraviolet light absorber was set at 0% (Comparative Examples 3 and 4), and when the amount of the (B) ultraviolet light scattering agent and the pigment grade titanium dioxide was set at 5% (Comparative Examples 5 and 6), a sufficient ultraviolet light protection effect (SPF) could not be obtained. Alternatively, when either one of the (A) ultraviolet light absorber and the (B) ultraviolet light scattering agent and the pigment grade titanium dioxide was mixed in an amount of 10% or more than 30%, finish and usability still remained undesirable, although the ultraviolet light protection effect could be obtained sufficiently (Comparative Examples 1, 2, 7, and 8).

Table 2 shows the results of the test for the dispersed state of titanium oxide when various dispersants (surfactants) were mixed. The evaluation of the dispersed state can be performed by measuring the viscosity. A lower viscosity can be evaluated as being better. The numerical value showing the mixing amount of each component in the table represents the numerical value in terms of mass %.

TABLE 2

| | | Test Example 1 | Test Example 2 | Test Example 3 | Test Example 4 | Test Example 5 | Test Example 6 | Test Example 7 | Test Example 8 |
|---|---|---|---|---|---|---|---|---|---|
| Volatile oil component | Cyclopentasiloxane | 67 | 70 | 67 | 67 | 67 | 67 | 67 | 67 |
| UV light scattering agent | Hydrophobized fine grain titanium oxide | 30 | 30 | 30 | 30 | 30 | 30 | 30 | 30 |
| Dispersant | Bis-butyl dimethicone polyglyceryl-3 | — | 3 | — | — | — | — | — | — |
| | PEG-9 polydimethylsiloxyethyl dimethicone | — | — | 3 | — | — | — | — | — |

TABLE 2-continued

|  | Test Example 1 | Test Example 2 | Test Example 3 | Test Example 4 | Test Example 5 | Test Example 6 | Test Example 7 | Test Example 8 |
|---|---|---|---|---|---|---|---|---|
| PEG-10 dimethicone | — | — | — | 3 | — | — | — | — |
| Lauryl PEG-9 polydimethylsiloxydimethicone | — | — | — | — | 3 | — | — | — |
| Isostearic acid | — | — | — | — | — | 3 | — | — |
| Sorbitan sesquiisostearate | — | — | — | — | — | — | 3 | — |
| Polyglyceryl-2 diisostearate | — | — | — | — | — | — | — | 3 |
| Total | 100 | 100 | 100 | 100 | 100 | 100 | 100 | 100 |
| Viscosity (mPa·s) | 1579 | 14 | 47.2 | 66.6 | 30.5 | 523 | 281 | 257 |

Viscosity measurement conditions: viscosity meter TVB-10M manufactured by Toki Sangyo Co., Ltd., viscosity value after 60 seconds at a rotation speed of 30 rpm, and a temperature of 25° C., the rotor No. was changed according to the viscosity value (to 100 mPa·s No. 1, 100 to 1000 mPa·s No. 2, 1000 to 10000 No. 3)

The results of Table 2 indicate as follows: the dispersant was preferably a silicone surfactant, and in particular, when bis-butyl dimethicone polyglyceryl-3 is mixed, high flowability could be kept even when titanium oxide is mixed in an amount of 10%.

Formulation Examples 1 to 5 of the liquid cosmetic for use in the cosmetic of the present invention cosmetic will be shown below as Examples. The mixing amounts are all expressed as the amounts in terms of mass % based on the amount of the liquid cosmetic.

TABLE 3

| Classification | Name | Formulation Example 1 Foundation | Formulation Example 2 BB cream | Formulation Example 3 Primer | Formulation Example 4 White powder | Formulation Example 5 Concealer |
|---|---|---|---|---|---|---|
| Volatile oil component | Cyclopentasiloxane | 27.52% | 28.895% | 30.75% | 22.750% | 22.770% |
| Compatible oil component | Isopropyl myristate | — | 2.00% | 5.00% | — | 2.00% |
|  | Pentaerythrityl tetraethyl hexanoate | 4.00% | 2.00% | — | 2.00% | 2.00% |
| Activator | PEG-10 dimethicone | 3.00% | 3.00% | 2.00% | 2.00% | 2.00% |
|  | Lauryl PEG-9 polydimethylsiloxy ethyl dimethicone | — | — | 2.00% | 2.00% | 1.00% |
|  | PEG-9 polydimethylsiloxy diethyl dimethicone | 1.50% | 1.50% | — | 1.00% | 1.50% |
| Dispersant | Bis-butyl dimethicone polyglyceryl-3 | 1.00% | 1.00% | 1.00% | 1.00% | 1.00% |
| Clay mineral | Distearyldimonium hectorite | 0.50% | 0.50% | 0.50% | 0.50% | 0.50% |
| Ultraviolet light absorber | Octylmethoxy cinnamate | 6.50% | 5.00% | 7.00% | 3.00% | 5.00% |
| Ultraviolet light scattering agent | Hydrophobized fine grain titanium oxide | 11.00% | 15.00% | 13.00% | 15.00% | 3.00% |
| Coloring material | Hydrophobized pigment grade titanium oxide | 7.00% | 2.00% | — | — | 20.00% |
|  | Hydrophobized iron oxide (red) | 0.430% | 0.130% | — | — | 1.350% |
|  | Hydrophobized iron oxide (yellow) | 0.790% | 0.220% | — | — | 2.100% |
|  | Hydrophobized iron oxide (black) | 0.010% | 0.005% | — | — | 0.030% |
| Spheroidal powder | Spheroidal powder | 3.00% | 5.00% | 10.00% | 20.00% | — |
| Water | Water | 23.000% | 23.000% | 23.000% | 28.000% | 32.000% |
| Moisturizing agent | Glycerin | 10.00% | 10.00% | 5.00% | 2.00% | 3.00% |
| Antiseptic agent | Paraben | 0.25% | 0.25% | 0.25% | 0.25% | 0.25% |
|  | Phenoxyethanol | 0.50% | 0.50% | 0.50% | 0.50% | 0.50% |
| Total |  | 100.000% | 100.000% | 100.000% | 100.000% | 100.000% |

The invention claimed is:

1. A cosmetic, comprising:
   a liquid cosmetic including:
   an (A) ultraviolet light absorber in an amount of 1 to 10 mass %,
   an (B1) ultraviolet light scattering agent in an amount of 3 to 13 mass %,
   a (B2) pigment grade titanium oxide in an amount of 7 to 20 mass %, and
   (C) a silicone surfactant being bis-butyl dimethicone polyglyceryl-3; and
   an impregnated body impregnated with the liquid cosmetic,
   the liquid cosmetic being configured to be taken from the impregnated body with a finger or an applicator for being applied to the skin.

2. The cosmetic according to claim 1,
   wherein the (A) ultraviolet light absorber is octylmethoxy cinnamate.

3. The cosmetic according to claim 1,
   wherein the (B1) ultraviolet light scattering agent is a fine grain titanium oxide or a fine grain zinc oxide.

4. The cosmetic according to claim 1,
   wherein the liquid cosmetic is a water-in-oil emulsified cosmetic.

5. The cosmetic according to claim 1,
   wherein the impregnated body is a fiber body, a foamed body, or a porous body.

6. The cosmetic according to claim 1,
   wherein the impregnated body impregnated with the liquid cosmetic is housed in a compact container having airtightness.

7. The cosmetic according to claim 1,
   wherein the applicator is a brush.

* * * * *